(12) United States Patent
Mason et al.

(10) Patent No.: US 7,914,563 B2
(45) Date of Patent: Mar. 29, 2011

(54) HEAT TRANSFER PAD HAVING OCCLUSION-RESISTANT PORTS

(75) Inventors: Jeffrey T. Mason, Escondido, CA (US); Mark E. Howard, San Diego, CA (US)

(73) Assignee: Breg, Inc., Vista, CA (US)

( * ) Notice: Subject to any disclaimer, the term of this patent is extended or adjusted under 35 U.S.C. 154(b) by 988 days.

(21) Appl. No.: 11/803,704

(22) Filed: May 14, 2007

(65) Prior Publication Data
US 2008/0288033 A1    Nov. 20, 2008

(51) Int. Cl.
*A61F 7/00* (2006.01)
(52) U.S. Cl. .......................................... 607/104; 108/96
(58) Field of Classification Search .................... 607/96, 607/104, 108–112, 114
See application file for complete search history.

(56) References Cited

U.S. PATENT DOCUMENTS

| | | |
|---|---|---|
| 2,726,658 A | 12/1955 | Chessey |
| 3,548,819 A | 12/1970 | Davis et al. |
| 3,683,902 A | 8/1972 | Artemenko et al. |
| 3,901,225 A | 8/1975 | Sconce |
| 4,706,658 A | 11/1987 | Cronin |
| 4,962,761 A | 10/1990 | Golden |
| 5,241,951 A | 9/1993 | Mason et al. |
| D345,609 S | 3/1994 | Mason et al. |
| D348,106 S | 6/1994 | Mason et al. |
| 5,417,720 A | 5/1995 | Mason et al. |
| 5,662,695 A | 9/1997 | Mason et al. |
| 2004/0210176 A1 | 10/2004 | Diana |

*Primary Examiner* — Thomas J Sweet
*Assistant Examiner* — Ryan Henderson
(74) *Attorney, Agent, or Firm* — Rodney F. Brown (57) ABSTRACT

A heat transfer pad includes a bladder and a pad port. The bladder has an outside perimeter, an inner face and an outer face enclosing a bladder interior. The pad port has a tubing segment with a proximal end which extends through the outside perimeter of the bladder into the bladder interior. A port seal is formed by bonding the inner and outer faces of the bladder to the proximal end of the tubing segment at a port bond point distal to the outside perimeter of the bladder in the bladder interior. The proximal end of the tubing segment is maintained unbonded to the inner and outer faces of the bladder between the port seal and the outside perimeter of the bladder, thereby defining a strain relief section of the bladder which resists occlusion of the pad port.

14 Claims, 8 Drawing Sheets

Fig. 9

HEAT TRANSFER PAD HAVING OCCLUSION-RESISTANT PORTS

TECHNICAL FIELD

The present invention relates generally to therapeutic treatment of bodily injuries and ailments by cooling or heating an affected region of the body of a patient, and more particularly, to a heat transfer pad having a non-ambient temperature heat transfer fluid circulated therethrough which is positioned on the affected region to cool or heat the region.

BACKGROUND OF THE INVENTION

Bodily injuries and ailments are commonly treated by applying a non-ambient temperature material to the affected region of the body. For example, a low temperature material, typically applied in the form of cold water, ice or a cold pack, may advantageously inhibit swelling in the region of the injury. A high temperature material, typically applied in the form of hot water, a hot pack or an active heating element, may advantageously reduce pain and promote healing. A number of splint devices are known in the art for applying non-ambient temperature materials to injured or otherwise ailing regions of the body as evidenced by U.S. Pat. No. 3,548,819 to Davis et al; U.S. Pat. No. 3,901,225 to Sconce; and U.S. Pat. No. 4,706,658 to Cronin. One disadvantage of such devices is that the low temperature materials become warmer as they remain in contact with the body during treatment and the body transfers heat to the low temperature materials. Conversely, high temperature materials become cooler as they transfer heat to the body. This disadvantage can be remedied by periodically replacing the non-ambient temperature materials. However, constant replenishment of these materials is cumbersome and inconvenient, and results in periodic treatment temperature fluctuations.

In response to this problem, a number of systems have been developed for continuously circulating a cooling fluid from a low temperature reservoir to a desired body location. Such systems are typified by U.S. Pat. No. 2,726,658 to Chessey; U.S. Pat. No. 3,683,902 to Artemenko et al; and U.S. Pat. No. 4,962,761 to Golden. These fluid circulation systems in general are relatively complex, rendering them costly to manufacture and maintain, as well as difficult to operate. Accordingly, the systems are not practical for widespread use.

U.S. Pat. No. 5,241,951 to Mason et al. incorporated herein by reference discloses a therapeutic treatment system which rectifies the shortcomings of the above-referenced fluid circulation systems. The therapeutic treatment system of U.S. Pat. No. 5,241,951 is relatively simple, rendering it less costly to manufacture and maintain and enabling greater ease of operation than the prior systems. The system of U.S. Pat. No. 5,241,951 includes a fluid reservoir, a submersible single-speed pump, a pliant heat transfer pad having pad inlet and outlet ports and an internal pad flowpath, system inlet and outlet lines connecting the internal pad flowpath to the pump via the pad inlet and outlet ports, and a user adjustable in-line flow control valve.

The therapeutic treatment system of U.S. Pat. No. 5,241,951 is operated by filling the fluid reservoir with a non-ambient temperature heat transfer fluid and submersing the pump in the heat transfer fluid. The heat transfer pad is positioned at a desired treatment region of the body, conformed to the contours of the treatment region, and mounted thereon. The pump is activated to deliver fresh heat transfer fluid from the fluid reservoir to the internal pad flowpath via the system inlet line and pad inlet port and to return spent heat transfer fluid from the internal pad flowpath to the fluid reservoir via the pad outlet port and system outlet line. The patient regulates the treatment temperature of the heat transfer pad by manually adjusting the flow control valve to control the flow rate of heat transfer fluid through the internal pad flowpath.

Specific examples of prior art heat transfer pads having utility in the therapeutic treatment system of U.S. Pat. No. 5,241,951 are disclosed in commonly-owned U.S. Pat. No. 5,417,720 to Mason et al. and U.S. Design Patents Des. 348, 106 and Des. 345,609 to Mason et al., all of which are incorporated herein by reference. A prior art heat transfer pad of the type disclosed in the above-listed patents is shown and described with reference to FIGS. 1 and 2. The heat transfer pad is generally designated 100 and includes a first pad port 102, a second pad port 104, and a bladder 106.

Figure 1:
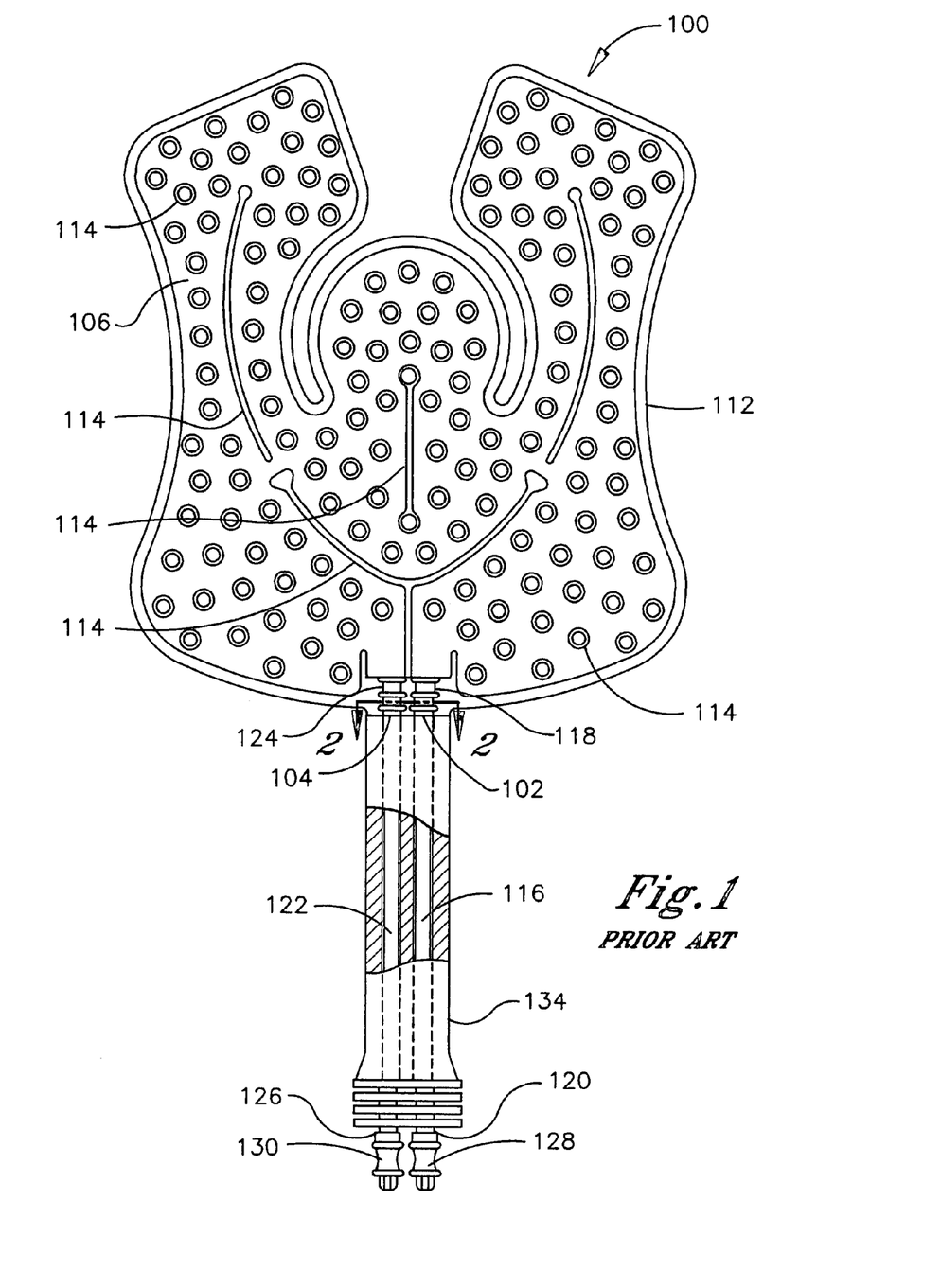
FIG. 1 is a detailed plan view of a prior art heat transfer pad having utility in a non-ambient temperature therapy system.
Figures 2, 3:
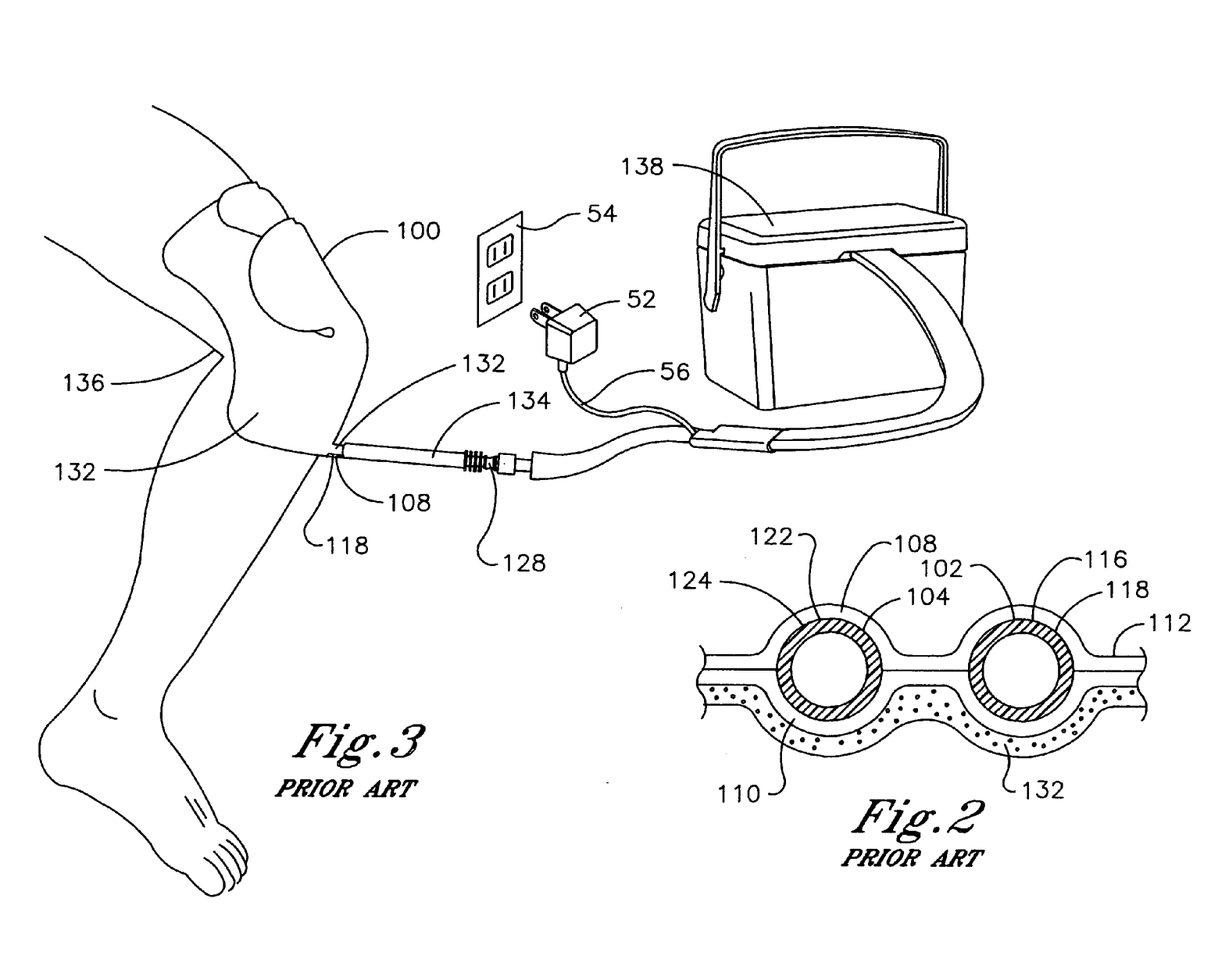
FIG. 2 is a cross-sectional view taken along line 2-2 in FIG. 1 of the pad inlet and outlet ports in the prior art heat transfer pad of FIG. 1.
FIG. 3 is a perspective view of the prior art heat transfer pad of FIG. 1 mounted on the knee of a patient.

The bladder 106 is a planar member comprising an inner sheet 108 and an outer sheet 110. The inner and outer sheets 108, 110 are each formed from a plastic film and are identically shaped to be laid one atop the other. The inner and outer sheets 108, 110 are peripherally bonded by conventional means such as welding to one another and to the first and second pad ports 102, 104 to define a peripheral seal 112. The inner and outer sheets 108, 110 are also periodically bonded together at a plurality of points interior to the peripheral seal 112 which are not contiguous with the peripheral seal 112 to define a plurality of flow diverters 114. The peripheral seal 112 and flow diverters 114 enclose and delineate a tortuous internal flowpath for a non-ambient temperature heat transfer fluid through the void space between the inner and outer sheets 108, 110 of the bladder 106.

The first and second pad ports 102, 104 are positioned side-by-side with the first pad port 102 being an inlet port and the second pad port 104 being an outlet port for the internal flowpath of the bladder 106. The first pad port 102 includes a first tubing segment 116 having a proximal end 118 and a distal end 120. The proximal end 118 extends between the peripheries of the inner and outer sheets 108, 110 of the bladder 106 which are permanently bonded to the outer wall of the proximal end 118, thereby maintaining the continuity of the peripheral seal 112 at the first pad port 102. The proximal end 118 is ribbed to strengthen the bond between the proximal end 118 and the inner and outer sheets 108, 110.

The second pad port 104 similarly includes a second tubing segment 122 having a proximal end 124 and a distal end 126. The proximal end 124 extends between the peripheries of the inner and outer sheets 108, 110 of the bladder 106 which are permanently bonded to the outer wall of the proximal end 124, thereby maintaining the continuity of the peripheral seal 112 at the second pad port 104. The proximal end 124 is ribbed to strengthen the bond between the proximal end 124 and the inner and outer sheets 108, 110. The proximal ends 118, 124 of the first and second tubing segments 116, 122 are open to the internal flowpath of the bladder 106, but are separated from direct fluid communication with one another by the flow diverters 114.

The distal ends 120, 126 of the first and second tubing segments 116, 122, respectively, extend away from the bladder 106 in the opposite direction as the proximal ends 118, 124. The distal ends 122, 126 have first and second port couplings 128, 130, respectively, positioned across them. The first and second port couplings 128, 130 are configured to cooperatively and releasably mate with first and second line couplings, respectively, included in the first and second system fluid circulation lines, respectively, which are not shown herein, but are shown and described in U.S. Pat. No. 5,241, 951.

The heat transfer pad 100 is further provided with insulating means to diminish heat transfer between the heat transfer pad 100 and the surrounding environment. In particular, an insulating foam sheet 132 is bonded to the outside face of the outer sheet 110 and an insulating port sheath 134 (shown partially cut away) extends between the first and second port couplings 128, 130 and the bladder 106 and covers the first and second tubing segments 116, 122.

The heat transfer pad 100 generally provides effective therapeutic treatment to the body when used in conjunction with the therapeutic treatment system of U.S. Pat. No. 5,241,951. Nevertheless, it has been found in some cases that the first and second pad ports 102, 104 are prone to occlusion when the heat transfer pad 100 is mounted on the body of a patient in conformance with the contours of the treatment region. For example, with reference to FIGS. 3 and 4, the heat transfer pad 100 is shown mounted on the flexed knee 136 of a patient. The fluid reservoir 138 is positioned at an elevated location relative to the heat transfer pad 100, which requires the user to angle the first and second tubing segments 116, 122 relative to the bladder 106 to achieve fluid communication between the first and second pad ports 102, 104 and the fluid reservoir 138.

Figure 4:
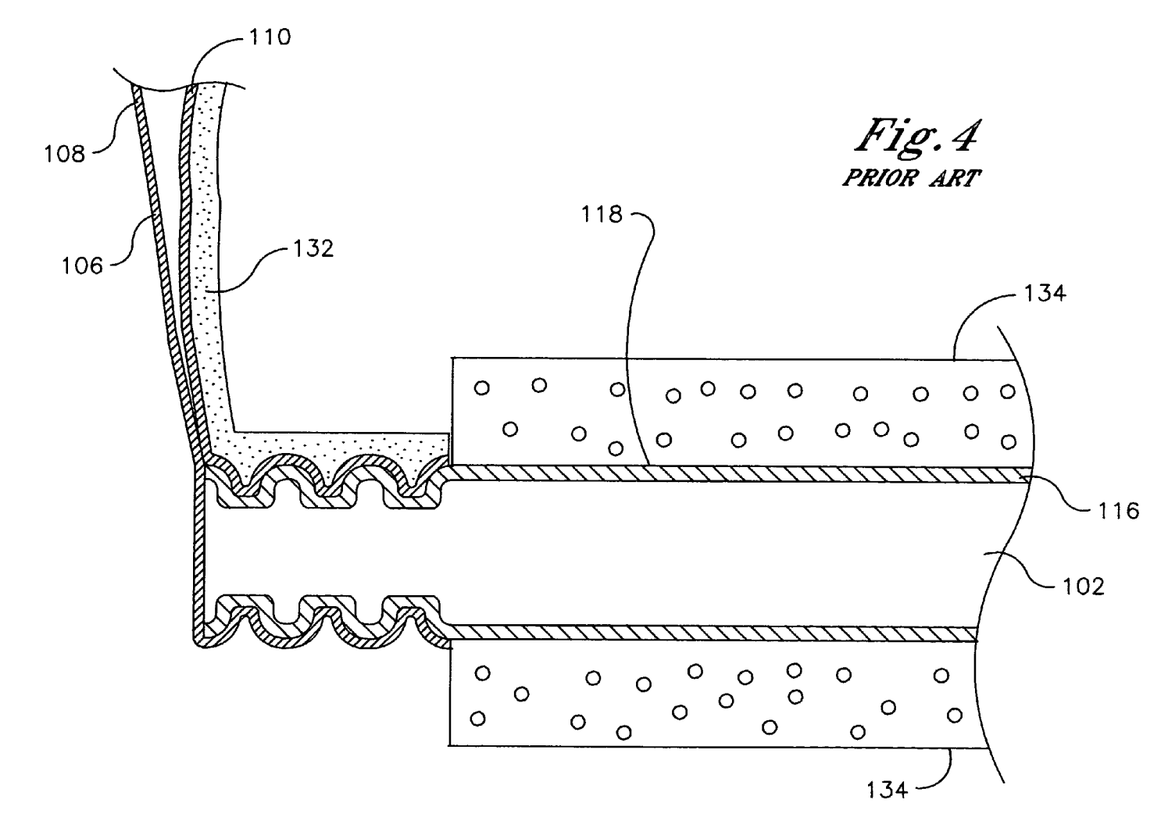
FIG. 4 is a cross-sectional view of the pad inlet port in the prior art heat transfer pad of FIG. 3 taken along the plane of FIG. 3, wherein the pad inlet port is in an occluded condition.

However, angling the first and second tubing segments 116, 122 flexes the bladder 106 near the openings of the respective proximal ends 118, 124 because the bladder 106 is substantially more flexible than the first and second tubing segments 116, 122 at the flexion point. When the first and second tubing segments 116, 122 are flexed at angles of about 90 degrees or more as shown, the bladder 106 becomes kinked or pinched near the openings of the respective proximal ends 118, 124, respectively, thereby occluding the first and second pad ports 102, 104. Thus, angling the first and second tubing segments 116, 122 relative to the bladder 106 impedes the flow of the heat transfer fluid through the internal pad flowpath and undesirably diminishes the effectiveness of the therapeutic treatment.

U.S. Pat. No. 5,662,695 to Mason et al. discloses a pad which is specifically constructed to resist occlusion due to pinching or kinking of the bladder in the region of the pad inlet and outlet ports. In particular, the peripheral region of the bladder adjacent to the pad inlet and outlet ports is constructed in a manner which renders the peripheral region more rigid than the remainder of the bladder. The rigidity is increased by affixing a patch to the surface of the bladder adjacent to the pad inlet and outlet ports which provides the patched area with a greater cross-sectional thickness than the remainder of the bladder.

The present invention recognizes the need for an alternate solution to the above-recited occlusion problem. Accordingly, it is generally an object of the present invention to provide a non-ambient temperature heat transfer pad having improved resistance to occlusion. More particularly, it is an object of the present invention to provide an improved non-ambient temperature heat transfer pad having pad inlet and outlet ports which are less prone to occlusion when the pad is mounted on the body of a patient during operation of a therapeutic treatment system. These objects and others are achieved in accordance with the invention described hereafter.

SUMMARY OF THE INVENTION

The present invention is a heat transfer pad which includes a bladder and a pad port. The bladder has an outside perimeter, an inner face and an outer face which enclose a bladder interior having an internal flowpath. The pad port has a tubing segment with a proximal end and a distal end. The distal end is positioned external to the bladder interior and the proximal end extends from the outside perimeter of the bladder an interior extension distance into the bladder interior. A port seal is formed by bonding the inner and outer faces of the bladder to the proximal end of the tubing segment at a port bond point distal to the outside perimeter of the bladder toward the bladder interior. However, the proximal end is maintained unbonded to the inner and outer faces of the bladder along an unbonded distance between the port bond point and the outside perimeter of the bladder, thereby defining a strain relief section of the bladder. The unbonded distance is preferably at least about 1 inch.

In accordance with a specific embodiment, the inner face of the bladder is an inner sheet and the outer face of the bladder is an outer sheet. The inner sheet is essentially continuously bonded to the outer sheet at the outside perimeter except proximal to where the proximal end of the tubing segment extends through the outside perimeter. Peripheral bonding the inner and outer sheets forms a peripheral seal which, in association with port seal, inner sheet and outer sheet, encloses the internal flowpath.

Another characterization of the invention is a heat transfer pad which includes a bladder, a first pad port and a second pad port. The bladder has an outside perimeter, an inner face and an outer face which encloses a bladder interior having an internal flowpath. The first pad port has a first tubing segment with a proximal end and a distal end. The distal end is positioned external to the bladder interior and the proximal end extends from the bladder perimeter a first interior extension distance into the bladder interior. A first port seal is formed by bonding the inner and outer faces of the bladder to the proximal end of the first tubing segment at a first port bond point distal to the outside perimeter of the bladder toward the bladder interior. However, the proximal end is maintained unbonded to the inner and outer faces of the bladder along a first unbonded distance between the first port bond point and the outside perimeter of the bladder.

The second pad port has a second tubing segment with a proximal end and a distal end. The distal end of the second tubing segment is positioned external to the bladder interior and the proximal end of the second tubing segment extends from the bladder perimeter a second interior extension distance into the bladder interior. A second port seal is formed by bonding the inner and outer faces of the bladder to the proximal end of the second tubing segment at a second port bond point distal to the outside perimeter of the bladder toward the bladder interior. However, the proximal end of the second tubing segment is maintained unbonded to the inner and outer faces of the bladder along a second unbonded distance between the second port bond point and the outside perimeter of the bladder. Maintaining the proximal ends of the first and second tubing segments unbonded to the inner and outer faces of the bladder along the first and second unbonded distances between the first and second port bond points and the outside perimeter of the bladder defines a strain relief section of the bladder.

Yet another characterization of the invention is a method for resisting occlusion in a heat transfer pad having a pad port and a bladder. The method includes placing an internal flowpath of the bladder in fluid communication with a fluid reservoir via the pad port. The pad port has a proximal end of a tubing segment extending into the internal flowpath of the bladder through an outside perimeter of the bladder. The proximal end is bonded to the bladder at a port bond point distal to the outside perimeter toward the internal flowpath. However, the proximal end is maintained unbonded to the bladder along an unbonded distance between the port bond point and the outside perimeter of the bladder, thereby defining a strain relief section of the bladder.

The method additionally includes conveying a heat transfer fluid from the fluid reservoir through the pad port and the internal flowpath. A bending force is applied to a distal end of the tubing segment extending away from the bladder which bends the tubing segment and the bladder along the strain relief section without substantially kinking or pinching the bladder at a location proximal to the junction of the tubing segment and the outside perimeter, thereby substantially enabling the pad port to resist occlusion.

The present invention will be further understood from the drawings and the following detailed description.

Embodiments of the invention and prior art are illustrated by way of example and not by way of limitation in the above-recited figures of the drawings, wherein like reference characters indicate the same or similar elements. It should be noted that common references to "an embodiment", "one embodiment", "an alternate embodiment", "a preferred embodiment", or the like herein are not necessarily references to the same embodiment.

DESCRIPTION OF PREFERRED EMBODIMENTS

Figure 5:
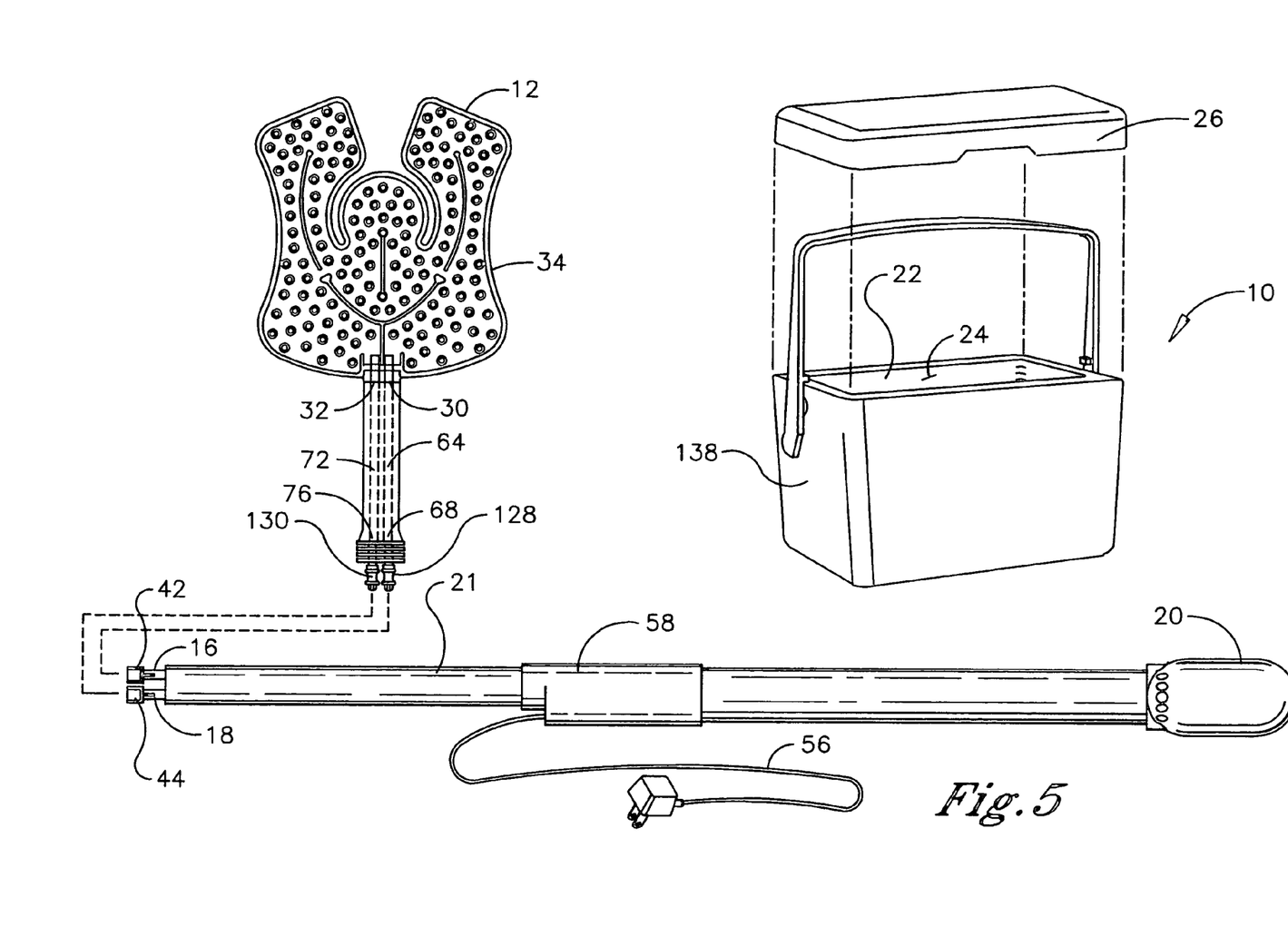
FIG. 5 is an exploded view of a non-ambient temperature therapy system in a disassembled state which includes the heat transfer pad of the present invention.
Figure 6:
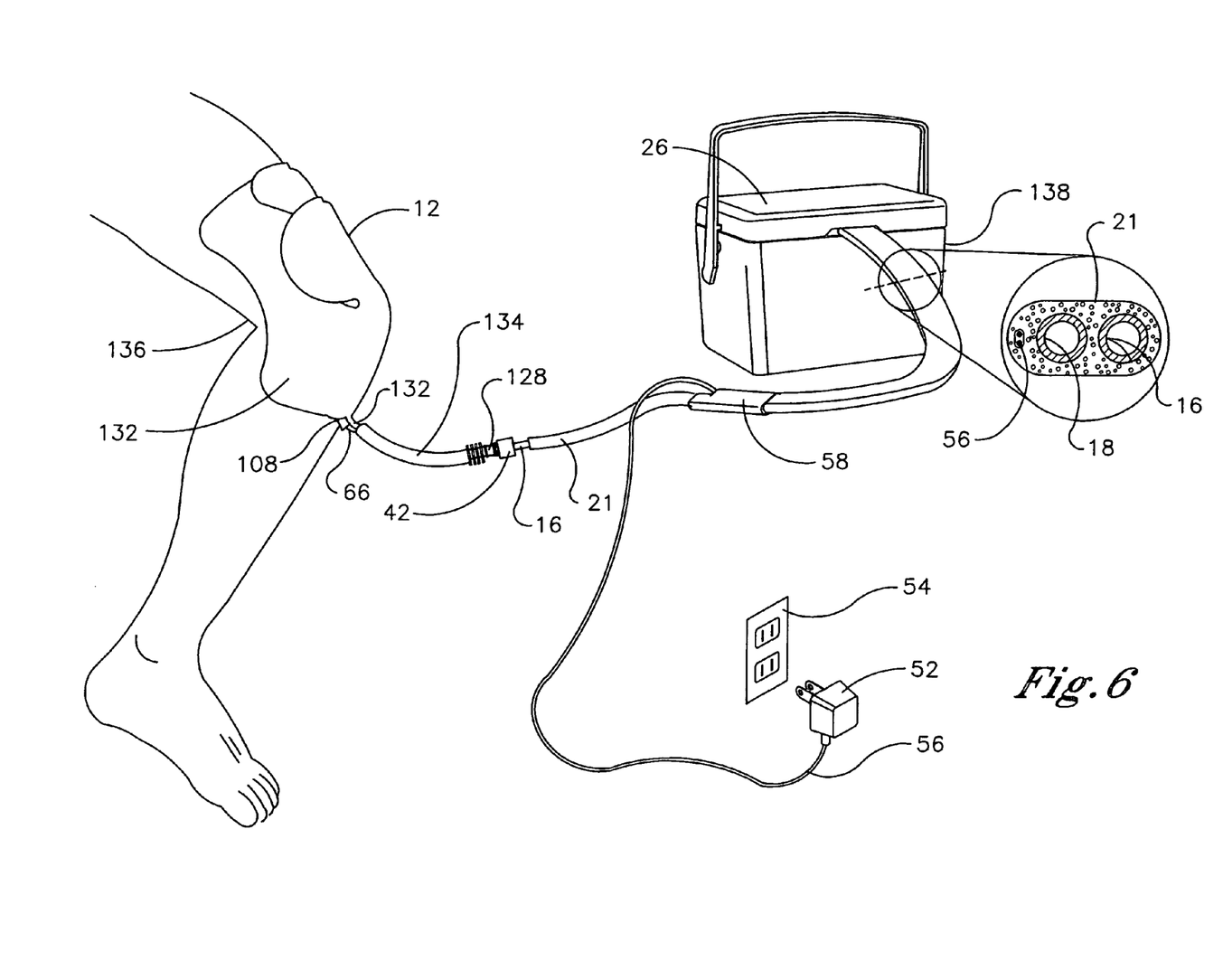
FIG. 6 is a perspective view of the non-ambient temperature therapy system of FIG. 5 in an assembled state, wherein the heat transfer pad of the present invention is operatively mounted on the knee of a patient.

Referring initially to FIG. 5, an example of a non-ambient temperature therapy system in which a heat transfer pad of the present invention can be employed is shown in a disassembled state and generally designated 10. The non-ambient temperature therapy system 10 comprises a heat transfer pad 12 of the present invention, the fluid reservoir 138, a first system fluid circulation line 16, a second system fluid circulation line 18, and a pump 20. Referring additionally to FIG. 6, the non-ambient temperature therapy system 10 is shown in an assembled state after a user has assembled the system 10 from the disassembled state. The user is typically a patient undergoing treatment with the non-ambient temperature therapy system 10 or a health care practitioner overseeing treatment of the patient with the system 10.

The term "non-ambient temperature" is used herein relative to the ambient body temperature of the patient. A high temperature treatment applies a non-ambient treatment temperature to the body which is greater than the ambient body temperature while a low temperature treatment applies a non-ambient treatment temperature to the body which is less than the ambient body temperature.

When the non-ambient temperature therapy system 10 is in the assembled state shown in FIG. 6, the heat transfer pad 12 and the fluid reservoir 138 are positioned a distance apart from one another with the first and second system fluid circulation lines 16, 18 extending in parallel between them. The first system fluid circulation line 16 functions as a pad inlet line, withdrawing a fresh non-ambient temperature heat transfer fluid from the fluid reservoir 138 and delivering the fresh non-ambient temperature heat transfer fluid to the heat transfer pad 12. Conversely, the second system fluid circulation line 18 functions as a pad outlet line, withdrawing the spent heat transfer fluid from the heat transfer pad 12 and delivering the spent heat transfer fluid to the fluid reservoir 138. The first and second system fluid circulation lines 16, 18 are each preferably formed from a continuous length of identical flexible tubing each having the essentially same inside diameter.

An insulating line sheath 21 extends essentially the length of the first and second system fluid circulation lines 16, 18 and covers the lines 16, 18, thereby enclosing the lines 16, 18 within a single integrated smooth tubular unit (as shown in the cross-section blow-up). The line sheath 21 is formed in its entirety from a supple material which renders the line sheath 21, in combination with the first and second system fluid circulation lines 16, 18, fully flexible. The line sheath 21 has a durable exterior skin and an insulating foam interior which minimizes heat transfer between the first system fluid circulation line 16 and the second system fluid circulation line 18 or between the first and second system fluid circulation lines 16, 18 and the surrounding environment 28. The line sheath 21 also prevents condensate formation on the exterior of the first and second system fluid circulation lines 16, 18.

The fluid reservoir 138 is a hollow fluid container, which includes means for a user to access the interior of the container, thereby enabling the user to manually add the non-ambient temperature heat transfer fluid in bulk to the fluid reservoir 138 when charging the non-ambient temperature therapy system 10 or to manually withdraw heat transfer fluid in bulk from the fluid reservoir 138 when draining the system 10. The fluid reservoir 138 is preferably a thermally-passive hollow fluid container having insulated walls 22 and a relatively wide accessible opening 24 at the top for addition or withdrawal of the heat transfer fluid. The preferred fluid reservoir 138 is additionally provided with a fitted removable lid 26, which enables the user to selectively cover the opening 24. Fitting the lid 26 across the opening 24 reduces the degree of heat transfer between the heat transfer fluid residing in the interior of the fluid reservoir 138 and the ambient atmosphere of the surrounding environment 28. The preferred fluid reservoir 138 described above is essentially the same or similar to a conventional picnic or beverage cooler.

The term "thermally-passive", as used herein, characterizes a structure which is free of any active structural cooling or heating elements, such as refrigeration coils, heating coils, or the like, which act on the heat transfer fluid to actively cool or heat the fluid. The entirety of the non-ambient temperature therapy system 10 is likewise preferably characterized as thermally-passive insofar as the system 10 in its entirety is preferably free of any active structural cooling or heating elements. Notwithstanding the above, it is within the scope of the present invention to place a passive cooling medium in the fluid reservoir 138, such as ice or the like, to passively cool the heat transfer fluid therein.

The heat transfer pad 12 includes a first pad port 30 which preferably functions as a pad inlet port, a second pad port 32 which preferably functions as a pad outlet port, and a bladder 34 which is positioned between the first and second pad ports 30, 32. The bladder 34 accommodates the first and second pad ports 30, 32 and encloses a tortuous internal flowpath for the non-ambient temperature heat transfer fluid extending through the bladder 34 from the first pad port 30 to the second pad port 32.

The pump 20 of the non-ambient temperature therapy system 10 is generally a means for driving the non-ambient temperature heat transfer fluid from the fluid reservoir 138 to the bladder 34 via the first system fluid circulation line 16 and the first pad port 30. The pump 20 is further a means for circulating the non-ambient temperature heat transfer fluid through the internal flowpath of the bladder 34 and for driving the heat transfer fluid from the bladder 34 to the fluid reservoir 138 via the second pad port 32 and second system fluid circulation line 18.

The pump 20 of the non-ambient temperature therapy system 10 can be selected from a number of pumps having differing structures and mechanisms of operation. For example, the pump 20 can inter alia be an axial pump, a centrifugal pump, a gear pump, or a reciprocating pump, each of which has its own distinct structure and mechanism of operation. A preferred pump has a single-speed pump motor and is termed a single-speed pump, which is defined herein as a pump having a pump motor which is permanently fixed at one set operating speed when pumping against a minimal downstream resistance to flow. The single-speed pump lacks means for the user to adjust or reset the set operating speed of the pump motor.

An exemplary pump having utility in the system 10 is a single-speed submersible axial pump driven by a dc-powered electric motor, such as generally disclosed in U.S. Pat. No. 5,241,951. The system 10 employs a transformer 52 upstream of the pump 20 which converts ac power from a conventional ac wall outlet 54 to dc power. A power line 56 conveys the dc power from the transformer 52 to a dc motor in the pump 20. The power line 56 is exposed as it extends between the transformer 52 and a power connector 58 mounted on the first and second system fluid circulation lines 16, 18. The power line 56 is enclosed within the line sheath 21 parallel to the first and second system fluid circulation lines 16, 18 (shown in FIG. 6) as the power line 56 extends from the power connector 58 to the pump 20.

Alternatively, the dc-powered pump 20 obtains dc power directly from a dc power source, such as an automobile battery or a portable external or internal battery pack consisting of one or more disposable dry cell batteries or rechargeable batteries. In another alternative, the pump is driven by an ac-powered electric motor which is directly connected to the ac wall outlet 54.

An alternate pump is one having a variable-speed pump motor. Such a pump is termed a variable-speed pump and is defined herein as a pump which includes means for the user to actively vary the set operating speed of the pump motor.

The distal ends of the first and second system fluid circulation lines 16, 18 are attached to the pump 20 and are in fluid communication with an internal pumping chamber (not shown) of the pump 20 which is open to the surrounding environment 28. The pump 20 and distal ends of the first and second system fluid circulation lines 16, 18 are operatively positioned in the interior of the fluid reservoir 138 and preferably submerged in the non-ambient temperature heat transfer fluid filling the interior of the fluid reservoir 138 when the non-ambient temperature therapy system 10 is in the assembled state. Accordingly, the first and second system fluid circulation lines 16, 18 are in fluid communication with the interior of the fluid reservoir 138. However, the fluid reservoir 138 is not physically connected to the pump 20 and the first and second system fluid circulation lines 16, 18. Alternately stated, the fluid reservoir 138 is structurally independent from the pump 20 and first and second system fluid circulation lines 16, 18. Although not shown, it is alternatively within the scope of the present invention to structurally integrate or otherwise physically connect the fluid reservoir 138 with the pump 20 and/or with the first and second system fluid circulation lines 16, 18.

Although the present invention is not limited to the positioning of the heat transfer pad 12 relative to the fluid reservoir 138, FIG. 6 shows a particular embodiment, wherein the heat transfer pad 12 is mounted on the flexed knee 136 of a patient while the fluid reservoir 138 is positioned at an elevated location relative to the heat transfer pad 12. Under these circumstances, it may be necessary to angle the first and second pad ports 30, 32 of the heat transfer pad 12 relative to the bladder 34 to place the first and second pad ports 30, 32 in fluid communication with the fluid reservoir 138 as required for operation of the therapeutic treatment system 10. The specific configuration of the first and second pad ports 30, 32 and their association with the bladder 34 as described below prevents or reduces the risk of occlusion of the first and second pad ports 30, 32 when it is desirable or necessary to flex or bend the first or second pad ports 30, 32 during operation of the therapeutic treatment system 10.

The first and second pad ports 30, 32 (described in greater detail below with reference to FIGS. 7-9) include the first and second port couplings 128, 130, which are positioned across the distal ends of the first and second pad ports 30, 32, respectively. The first and second port couplings 128, 130 are configured to cooperatively and releasably mate with first and second line couplings 42, 44, respectively, which are included in the first and second system fluid circulation lines 16, 18, respectively, and are positioned across the open proximal ends of the first and second system fluid circulation lines 16, 18. The terms "proximal end" and "distal end" are used herein relative to the interior of the bladder 34. The "proximal end" is more proximal to the interior of the bladder 34 and the "distal end" is more distal to the interior of the bladder 34. The couplings 128, 130, 42, 44 are preferably snap-action locking couplings which are selectively manually releasable.

The first and second port couplings 128, 130 are male couplings and the first and second line couplings 42, 44 are female couplings. Although not shown, the first and second port couplings 128, 130 are alternatively configured as female couplings and the first and second line couplings 42, 44 are configured as male couplings. Mating the first port coupling 128 with the first line coupling 42 and the second port coupling 130 with the second line coupling 44 forms a connective joint between the heat transfer pad 12 and first and second system fluid circulation lines 16, 18. The joint provides fluid communication between the first and second pad ports 30, 32 and the first and second system fluid circulation lines 16, 18, respectively, as well as between the first and second system fluid circulation lines 16, 18 and the internal flowpath of the bladder 34 which is integral with the first and second pad ports 30, 32.

Each first and second port coupling 128, 130 also includes an integral shutoff valve element which restricts access to the internal flowpath of the bladder 34 from the surrounding environment 28 via the first and second pad ports 30, 32 when the first and second port couplings 128, 130 are unmated. As such, the shutoff valve element is normally biased in the closed position by a cooperative biasing means, such as a spring or the like, when the first and second port couplings 128, 130 are unmated. However, mating the first port coupling 128 with the first line coupling 42 and the second port coupling 130 with the second line coupling 44 brings the first and second line couplings 42, 44 into engagement with the shutoff valve element, thereby actively transitioning the shutoff valve element to the open position. When the shutoff valve element is in the open position, the shutoff valve element and associated biasing means do not substantially impede flow through the first and second port couplings 128, 130.

Figure 7:
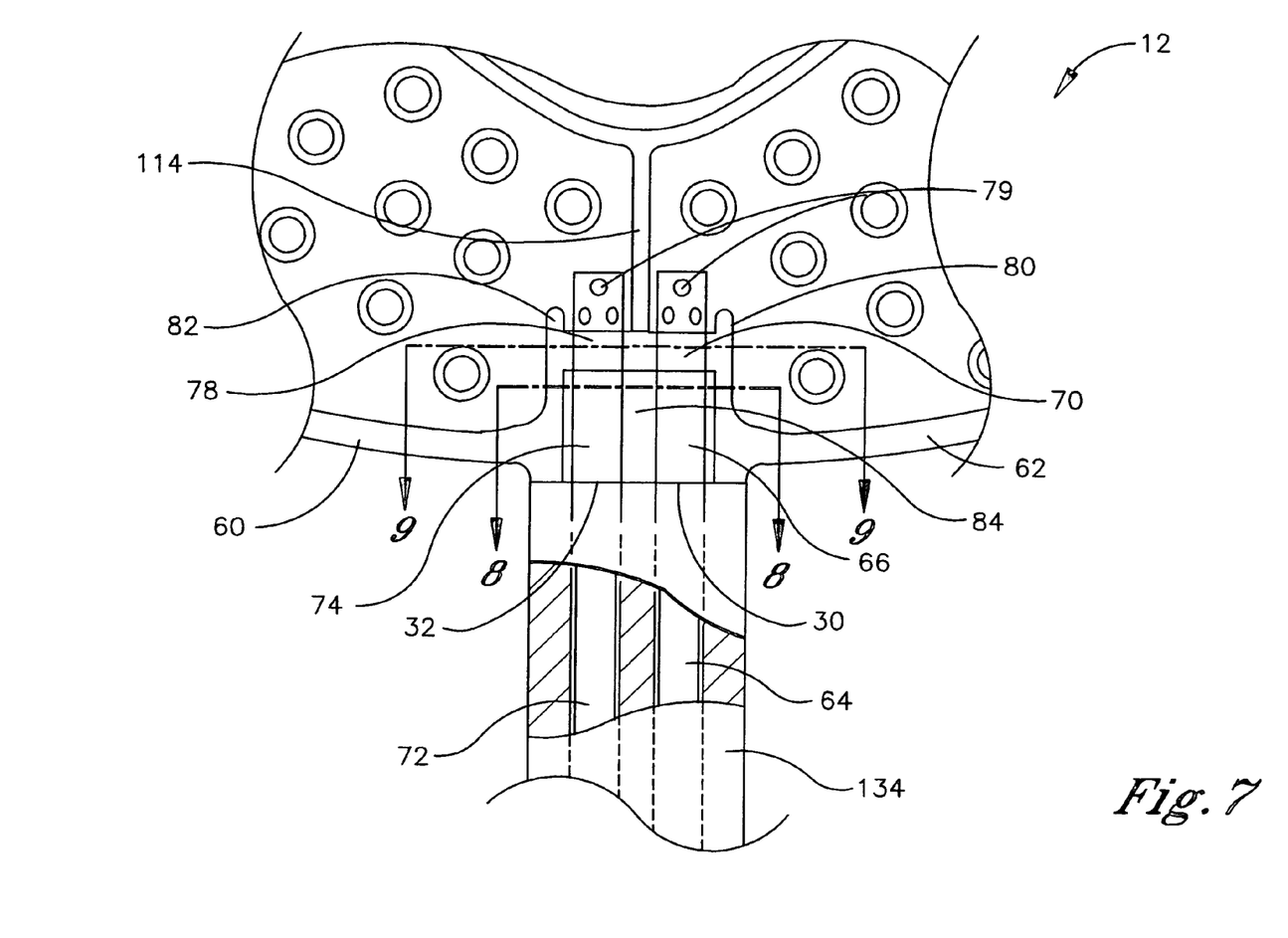
FIG. 7 is a detailed plan view of the pad inlet and outlet ports of the heat transfer pad of the present invention which is included in the non-ambient temperature therapy system of FIGS. 5 and 6.
Figure 8:
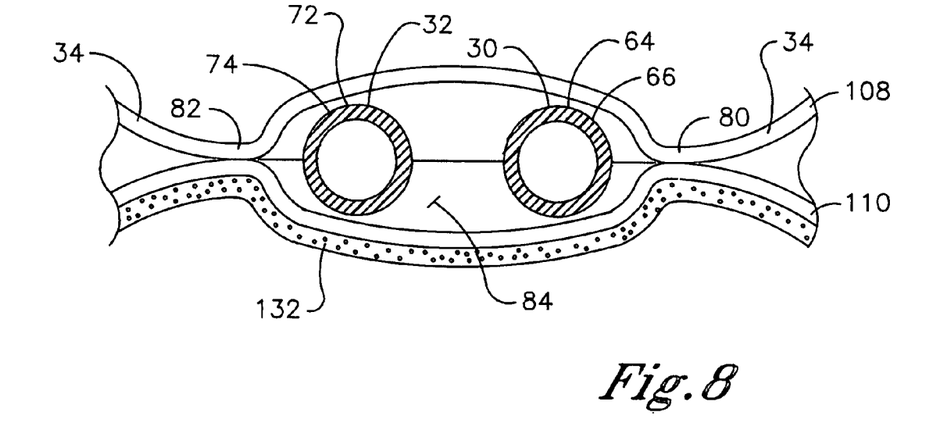
FIG. 8 is a cross-sectional view taken along line 8-8 in FIG. 7 of the pad inlet and outlet ports in the heat transfer pad of FIG. 7.
Figure 9:
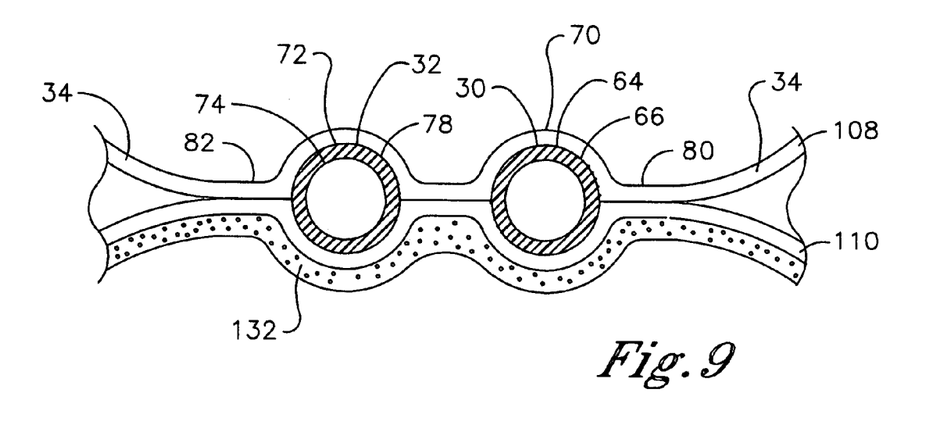
FIG. 9 is a cross-sectional view taken along line 9-9 in FIG. 7 of the pad inlet and outlet ports in the heat transfer pad of FIG. 7.

The heat transfer pad 12 is essentially the same as the heat transfer pad 100 of FIG. 1 except for the configuration of the first and second pad ports 30, 32 and their cooperative association with the bladder 34. Referring to FIGS. 7-9, details of the first and second pad ports 30, 32 and their cooperative association with the bladder 34 are shown. The bladder 34 is a planar member comprising the inner and outer sheets 108, 110 both of which are formed from a thin, flexible, heat-conductive, pliable, polyurethane film. The terms "inner sheet" and "outer sheet" are used herein relative to the body of the patient. The "inner sheet" is more proximal to the body and the "outer sheet" is more distal to the body when the heat transfer pad 12 is mounted on the body of the patient.

The inner and outer sheets 108, 110 are fixably and permanently bonded to one another along their entire peripheries 60 except at the location of the first and second pad ports 30, 32 as described below. Bonding the peripheries 60 to one another defines a peripheral seal 62 extending around the outside perimeter of the bladder 34, but discontinuous at the first and second pad ports 30, 32. The bladder 34 also includes the flow diverters 114 as described above with reference to FIG. 1.

The first and second pad ports 30, 32 are positioned side-by-side at the outside perimeter of the bladder 34. The first pad port 30 includes a first tubing segment 64 having a proximal end 66 and a distal end 68. The proximal end 66 of the first tubing segment 64 extends between the inner and outer sheets 108, 110 into the interior of the bladder 34 and is open to the internal flowpath of the bladder 34. In particular, the proximal end 66 extends from the peripheries 60 of the inner and outer sheets 108, 110 and correspondingly from the outside perimeter of the bladder 34 a first interior extension distance into the interior of the bladder 34. The distal end 68 of the first tubing segment 64 extends away from the outside perimeter of the bladder 34 in the opposite direction as the proximal end 66.

The inner and outer sheets 108, 110 of the bladder 34 are fixably and permanently bonded to the outer wall of the proximal end 66 by a first port seal 70 which is positioned at a first port bond point distal to the peripheries 60 of the inner and outer sheets 108, 110 and correspondingly distal to the outside perimeter of the bladder 34 toward the interior of the bladder 34. The inner and outer sheets 108, 110 of the bladder 34 are maintained unbonded to the outer wall of the proximal end 66 along a first unbonded distance which extends from the peripheries 60 of the inner and outer sheets 108, 110 (and correspondingly from the outside perimeter of the bladder 34) to the first port seal 70.

As an example, the first interior extension distance is about 3 inches. Thus, the opening of the proximal end 66 is positioned in the interior of the bladder 34 about 3 inches from the outside perimeter of the bladder 34. The first unbonded distance is about 2 inches. Thus, the first port bond point is about 2 inches from the outside perimeter of the bladder 34 in the interior of the bladder 34.

The second pad port 32 similarly includes a second tubing segment 72 having a proximal end 74 and a distal end 76. The construction of the first and second tubing segments 66, 72 is substantially less flexible than the construction of the inner and outer sheets 108, 110 of the bladder 34. The proximal end 74 of the second tubing segment 72 extends between the inner and outer sheets 108, 110 into the interior of the bladder 34 and is open to the internal flowpath of the bladder 34. In particular, the proximal end 74 extends from the peripheries 60 of the inner and outer sheets 108, 110 and correspondingly from the outside perimeter of the bladder 34 a second interior extension distance into the interior of the bladder 34. The second interior extension distance is preferably about the same as the first interior extension distance. The distal end 76 of the second tubing segment 72 extends away from the outside perimeter of the bladder 34 in the opposite direction as the proximal end 74. The first and second port couplings 128, 130 are positioned across the distal ends 68, 76 of the first and second tubing segments 64, 72, respectively, in the manner described above.

The inner and outer sheets 108, 110 of the bladder 34 are fixably and permanently bonded to the outer wall of the proximal end 74 by a second port seal 78 which is positioned at a second port bond point preferably adjacent to the first port bond point and, in any case, distal to the peripheries 60 of the inner and outer sheets 108, 110 and correspondingly distal to the outside perimeter of the bladder 34 toward the interior of the bladder 34. The inner and outer sheets 108, 110 of the bladder 34 are maintained unbonded to the outer wall of the proximal end 74 along a second unbonded distance which extends from the peripheries 60 of the inner and outer sheets 108, 110 (and correspondingly from the outside perimeter of the bladder 34) to the second port seal 78. The second unbonded distance is preferably about the same as the first unbonded distance which in the present example is about 2 inches. In any case, the first and second unbonded distances are each preferably at least about 1 inch.

Additional flow apertures 79 are optionally provided through the walls of the proximal ends 66, 74 of the first and second tubing segments 64, 72, respectively, at points past the first and second port seals 70, 78, respectively, more internal to the bladder 34. The flow apertures 79 facilitate fluid flow into or out of the proximal ends 66, 74. Although the proximal ends 66, 74 of the first and second tubing segments 64, 72, respectively, are shown in the present embodiment as extending past the first and second port seals 70, 78, respectively, it is alternatively within the scope of the present invention to terminate the proximal ends 66, 74 at the first and second port seals 70, 78 such that the openings of the proximal ends 66, 74 are positioned at, rather than past, the first and second port seals 70, 78.

The tortuous internal flowpath for the non-ambient temperature heat transfer fluid through the void spaces between the inner and outer sheets 108, 110 of the bladder 34 is enclosed and delineated inter alia by the inner and outer sheets 108, 110, the peripheral seal 62, the first and second port seals 70, 78, and the flow diverters 114. The integrity of the internal flowpath is maintained at the outside edges of the first and second port seals 70, 78 by providing the peripheral seal 62 with first and second seal extensions 80, 82 which extend adjacent to the outside edges of the proximal ends 66, 74, respectively, from the peripheries 60 of the inner and outer sheets 108, 110 and merge with the first and second port seals 70, 78, respectively. It is further noted that the junction of the first and second port seals 70, 78 is sealed to prevent fluid flow therebetween.

The section of the bladder 34 extending between the outside perimeter of the bladder 34 and the first and second port seals 70, 78 is termed the strain relief section 84 of the bladder 34. In accordance with the present example, the strain relief section 84 has a length of about 2 inches. The proximal ends 66, 74 of the first and second tubing segments 64, 72 are unattached from the inner and outer sheets 108, 110 along the length of the strain relief section 84 which enables the first and second pad ports 30, 32 to resist occlusion due to pinching or kinking of the bladder 34 near the first and second pad ports 30, 32. For example, when the first and second tubing segments 64, 72 are angled relative to the bladder 34 as described below.

The heat transfer pad 12 is further provided with the insulating foam sheet 132 and the port sheath 134. The insulating foam sheet 132 is bonded to the outside face of the outer sheet 110 to insulate the bladder 34 from the surrounding environment 28. The insulating port sheath 134 (shown partially cut away) extends between the first and second port couplings 128, 130 and the bladder 34 and covers the first and second tubing segments 64, 72. The port sheath 134 is formed in its entirety from a supple material which renders the port sheath 134, in combination with the first and second tubing segments 64, 72, flexible. The port sheath 134 has a durable exterior skin and an insulating foam interior which diminishes heat transfer between the first tubing segment 64 and the second tubing segment 72 or between the first and second tubing segments 64, 72 and the surrounding environment. The port sheath 134 also prevents condensate formation on the exterior of the first and second tubing segments 64, 72.

Figure 10:
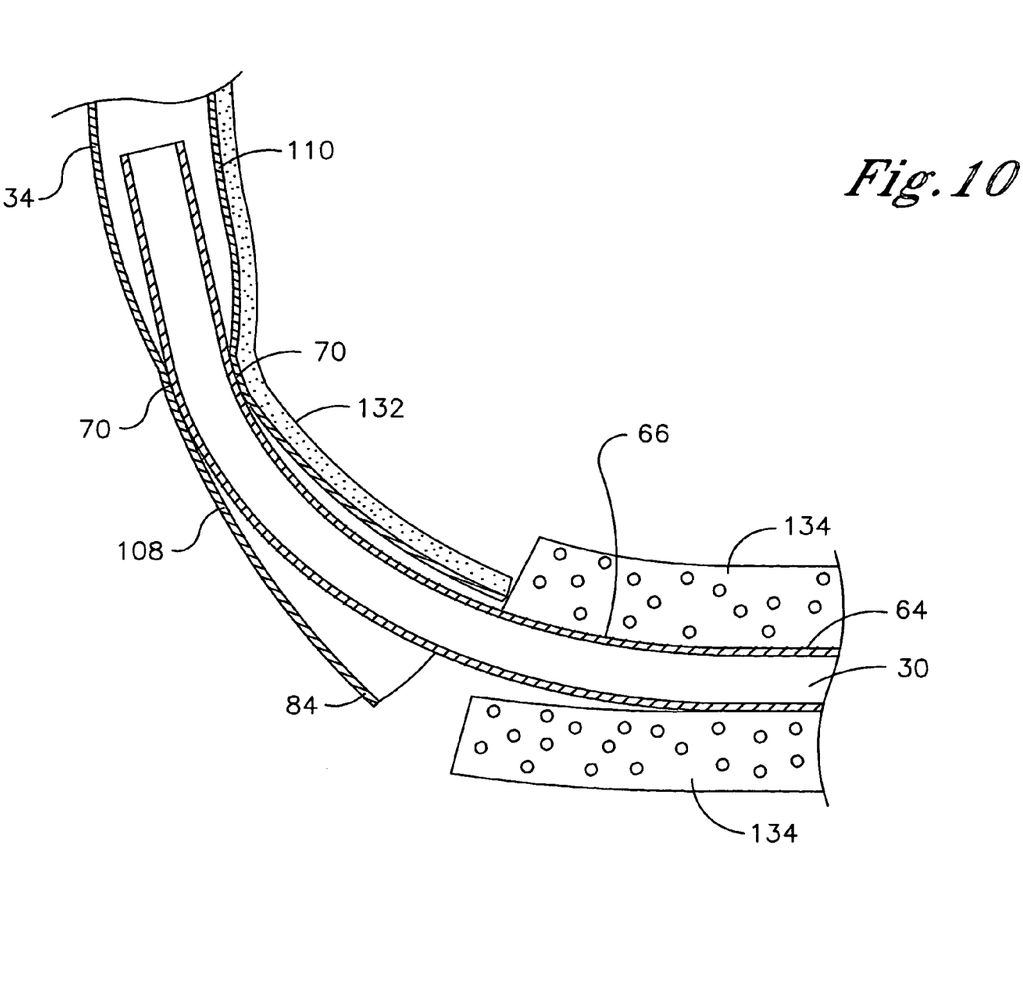
FIG. 10 is a cross-sectional view of the pad inlet port in the heat transfer pad of FIG. 6 taken along the plane of FIG. 6, wherein the pad inlet port is in an unobstructed condition.

With reference to FIG. 10, it is shown that the first and second pad ports 30, 32 resist occlusion when the heat transfer pad 12 is mounted on the body of a patient in conformance with the contours of the treatment region. For example, when the heat transfer pad 12 is mounted on the flexed knee 136 of a patient as shown in FIG. 6 while the fluid reservoir 138 is positioned at an elevated location relative to the heat transfer pad 12, it is necessary to angle the first and second tubing segments 64, 72 relative to the bladder 34 to place the first and second pad ports 30, 32 of the heat transfer pad 12 in fluid communication with the fluid reservoir 138 for operation of the therapeutic treatment system.

Angling of the first and second tubing segments 64, 72 is typically achieved by applying a bending force to the distal ends 68, 76 of the first and second tubing segments 64, 72, respectively. However, occlusion of the first and second pad ports 30, 32 is substantially avoided even when the first and second tubing segments 64, 72 are angled upward under the bending force because the inner and outer sheets 108, 110 are not bonded to the first and second tubing segments 64, 72 at their peripheries 60, thereby providing the bladder 34 with the strain relief section 80. The strain relief section 80 enables the first and second tubing segments 64, 72 to flex in cooperation with the bladder 34 at the outside perimeter of the bladder 34 when the first and second tubing segments 64, 72 are angled to essentially prevent the bladder 34 from pinching or kinking near the openings of the first and second tubing segments 64, 72 and correspondingly to prevent occlusion of the first and second pad ports 30, 32.

While the forgoing preferred embodiments of the invention have been described and shown, it is understood that alternatives and modifications, such as those suggested and others, may be made thereto and fall within the scope of the invention.

We claim:

1. A heat transfer pad comprising:
 a bladder having an outside perimeter, an inner face and an outer face enclosing a bladder interior, said bladder interior having an internal flowpath;
 a pad port having a tubing segment with a proximal end and a distal end, wherein said distal end is outside said bladder interior and said proximal end extends through said outside perimeter an interior extension distance into said bladder interior; and
 a port seal formed by bonding said inner and outer faces of said bladder to said proximal end at a port bond point away from said outside perimeter of said bladder toward said bladder interior, wherein said proximal end is maintained unbonded to said inner and outer faces of said bladder along an unbonded distance between said port bond point and said outside perimeter of said bladder, thereby defining a strain relief section of said bladder.

2. The heat transfer pad of claim 1, wherein said inner face of said bladder is an inner sheet and said outer face of said bladder is an outer sheet, said inner sheet being essentially continuously bonded to said outer sheet at said outside perimeter to form a peripheral seal except proximal to where said proximal end extends through said outside perimeter.

3. The heat transfer pad of claim 2, wherein said peripheral seal and said port seal enclose said internal flowpath.

4. The heat transfer pad of claim 1, wherein said inner and outer faces of said bladder are substantially more flexible than said tubing segment.

5. The heat transfer pad of claim 1, wherein said unbonded distance is at least about 1 inch.

6. The heat transfer pad of claim 2, wherein said pad port is a first pad port, said tubing segment is a first tubing segment, said port seal is a first port seal, said interior extension distance is a first interior extension distance, said port bond point is a first port bond point, and said unbonded distance is a first unbonded distance, said heat transfer pad further comprising a second pad port adjacent to said first pad port, said second pad port having a second tubing segment with a proximal end and a distal end, wherein said distal end of said second tubing segment is outside said bladder interior and said proximal end of said second tubing segment extends through said outside perimeter a second interior extension distance into said bladder interior, and a second port seal formed by bonding said inner and outer faces of said bladder to said proximal end of said second tubing segment at a second port bond point away from said outside perimeter of said bladder toward said bladder interior, wherein said proximal end of said second tubing segment is maintained unbonded to said inner and outer faces of said bladder along a second unbonded distance between said second port bond point and said outside perimeter of said bladder included in said strain relief section of said bladder.

7. The heat transfer pad of claim 6, wherein said peripheral seal and said first and second port seals enclose said internal flowpath.

8. A heat transfer pad comprising:
 a bladder having an outside perimeter, an inner face and an outer face enclosing a bladder interior;

a first pad port having a first tubing segment with a proximal end and a distal end, wherein said distal end of said first tubing segment is outside said bladder interior and said proximal end of said first tubing segment extends from said bladder perimeter a first interior extension distance into said bladder interior;

a first port seal formed by bonding said inner and outer faces of said bladder to said proximal end of said first tubing segment at a first port bond point away from said outside perimeter of said bladder toward said bladder interior, wherein said proximal end of said first tubing segment is maintained unbonded to said inner and outer faces of said bladder along a first unbonded distance between said first port bond point and said outside perimeter of said bladder;

a second pad port having a second tubing segment with a proximal end and a distal end, wherein said distal end of said second tubing segment is outside said bladder interior and said proximal end of said second tubing segment extends from said bladder perimeter a second interior extension distance into said bladder interior; and a second port seal formed by bonding said inner and outer faces of said bladder to said proximal end of said second tubing segment at a second port bond away from said outside perimeter of said bladder toward said bladder interior, wherein said proximal end of said second tubing segment is maintained unbonded to said inner and outer faces of said bladder along a second unbonded distance between said second port bond point and said outside perimeter of said bladder, further wherein maintaining said proximal ends of said first and second tubing segments unbonded to said inner and outer faces of said bladder along said first and second unbonded distances between said first and second port bond points and said outside perimeter of said bladder defines a strain relief section of said bladder.

9. The heat transfer pad of claim 8, wherein said inner face of said bladder is an inner sheet and said outer face of said bladder is an outer sheet, said inner sheet being essentially continuously bonded to said outer sheet at said outside perimeter to form a peripheral seal except where said proximal ends of said first and second tubing segments extend through said outside perimeter.

10. The heat transfer pad of claim 9, wherein said peripheral seal and said first and second port seals enclose said internal flowpath.

11. The heat transfer pad of claim 8, wherein said inner and outer faces of said bladder are substantially more flexible than said first and second tubing segments.

12. The heat transfer pad of claim 8, wherein said first and second unbonded distances are at least about 1 inch each.

13. The heat transfer pad of claim 8, wherein said first pad port is a pad inlet port.

14. The heat transfer pad of claim 8, wherein said second pad port is a pad outlet port.

* * * * *